US008899556B2

(12) United States Patent
Love et al.

(10) Patent No.: US 8,899,556 B2
(45) Date of Patent: Dec. 2, 2014

(54) SYSTEMS AND METHODS FOR GENERATION OF HYDROGEN PEROXIDE VAPOR

(75) Inventors: Adam H. Love, Berkeley, CA (US); Joel Del Eckels, Livermore, CA (US); Alexander K. Vu, Dublin, CA (US); Armando Alcaraz, Livermore, CA (US); John G. Reynolds, San Ramon, CA (US)

(73) Assignee: Lawrence Livermore National Security, LLC., Livermore, CA (US)

( * ) Notice: Subject to any disclaimer, the term of this patent is extended or adjusted under 35 U.S.C. 154(b) by 483 days.

(21) Appl. No.: 12/271,163

(22) Filed: Nov. 14, 2008

(65) Prior Publication Data

US 2009/0148379 A1 Jun. 11, 2009

Related U.S. Application Data

(60) Provisional application No. 60/988,371, filed on Nov. 15, 2007.

(51) Int. Cl.
| | | |
|---|---|---|
| C01B 15/00 | (2006.01) | |
| C01B 15/01 | (2006.01) | |
| C01B 15/013 | (2006.01) | |

(52) U.S. Cl.
CPC ............. *C01B 15/01* (2013.01); *C01B 15/013* (2013.01)
USPC .......................................... 261/74

(58) Field of Classification Search
USPC ................. 261/119.1, 121.1, 122.1
See application file for complete search history.

(56) References Cited

U.S. PATENT DOCUMENTS

| | | | | |
|---|---|---|---|---|
| 2,777,749 | A * | 1/1957 | Young | 8/111 |
| 5,340,987 | A * | 8/1994 | Eckles et al. | 250/345 |
| 5,508,009 | A | 4/1996 | Rickloff et al. | 422/292 |
| 5,996,397 | A * | 12/1999 | Mettes | 73/29.01 |
| 6,495,100 | B1 * | 12/2002 | Lin et al. | 422/29 |
| 7,640,782 | B2 * | 1/2010 | Hill | 73/1.02 |
| 2003/0007916 | A1 * | 1/2003 | Khorzad et al. | 422/305 |
| 2003/0049165 | A1 * | 3/2003 | Yamamoto et al. | 422/28 |
| 2003/0164091 | A1 * | 9/2003 | Hill et al. | 95/90 |
| 2006/0040152 | A1 * | 2/2006 | Wood | 429/19 |
| 2006/0131161 | A1 * | 6/2006 | Towler | 204/175 |

FOREIGN PATENT DOCUMENTS

JP        2006288647 A  * 10/2006

OTHER PUBLICATIONS

VHP®MD Series Sterilization System http://www.steris.com/explore/view_product$_{13}$ page.cfm?productid=157, Oct. 31, 2008.

* cited by examiner

*Primary Examiner* — Melissa Swain
(74) *Attorney, Agent, or Firm* — Dominic M. Kotab

(57) ABSTRACT

A system according to one embodiment includes a moisture trap for drying air; at least one of a first container and a second container; and a mechanism for at least one of: bubbling dried air from the moisture trap through a hydrogen peroxide solution in the first container for producing a hydrogen peroxide vapor, and passing dried air from the moisture trap into a headspace above a hydrogen peroxide solution in the second container for producing a hydrogen peroxide vapor. A method according one embodiment includes at least one of bubbling dried air through a hydrogen peroxide solution in a container for producing a first hydrogen peroxide vapor, and passing dried air from the moisture trap into a headspace above the hydrogen peroxide solution in a container for producing a second hydrogen peroxide vapor. Additional systems and methods are also presented.

22 Claims, 2 Drawing Sheets

SYSTEMS AND METHODS FOR GENERATION OF HYDROGEN PEROXIDE VAPOR

RELATED APPLICATIONS

This application claims priority to provisional U.S. application Ser. No. 60/988,371 filed on Nov. 15, 2007, which is herein incorporated by reference.

The United States Government has rights in this invention pursuant to Contract No. DE-AC52-07NA27344 between the United States Department of Energy and Lawrence Livermore National Security, LLC for the operation of Lawrence Livermore National Laboratory.

FIELD OF THE INVENTION

The present invention relates to hydrogen peroxide vapor generators, and more particularly to a hydrogen peroxide vapor generator and use thereof in the testing and calibration of hydrogen peroxide detectors.

BACKGROUND

In the near future, many airports will have detector platforms in place to screen for the presence of hydrogen peroxide vapor. Various hydrogen peroxide vapor detection systems are currently being evaluated for screening of liquids transport through security screening. These detection systems would benefit from improved ways to test the quality assurance and quality control of the detection platform in order to assure the detection system is performing as expected. Most conventional hydrogen peroxide vapor generator platforms cannot produce low concentration hydrogen peroxide vapor of the type that the airport detector platforms will be required to screen for, in order to accomplish their security function. Therefore, a method or device which is capable of producing a known and consistent low concentration hydrogen peroxide vapor is desirable to perform quality assurance/quality control tests on the airport hydrogen peroxide vapor detector platforms.

SUMMARY

A system according to one embodiment includes a moisture trap for drying air; at least one of a first container and a second container; and a mechanism for at least one of: bubbling dried air from the moisture trap through a hydrogen peroxide solution in the first container for producing a hydrogen peroxide vapor, and passing dried air from the moisture trap into a headspace above a hydrogen peroxide solution in the second container for producing a hydrogen peroxide vapor.

A hydrogen peroxide vapor generator according to another embodiment includes a moisture trap for drying air; a first aqueous hydrogen peroxide solution container having an inlet fluidically in line with the moisture trap to receive dry air therefrom by being bubbled through the aqueous hydrogen peroxide solution for producing higher concentration hydrogen peroxide vapor, and an outlet for availing the higher concentration hydrogen peroxide vapor; a second aqueous hydrogen peroxide solution container having an inlet fluidically in line with the moisture trap to receive dry air therefrom by being flowed into a headspace above the aqueous hydrogen peroxide solution for producing lower concentration hydrogen peroxide vapors and an outlet for availing the lower concentration hydrogen peroxide vapor; and a switch valve for selectively channeling the dry air flow to at least one of the first and second containers.

A method according to yet another embodiment includes at least one of bubbling dried air through a hydrogen peroxide solution in a container for producing a first hydrogen peroxide vapor, and passing dried air from the moisture trap into a headspace above the hydrogen peroxide solution in a container for producing a second hydrogen peroxide vapor.

A method in a further embodiment includes adding a hydrogen peroxide solution to a container; causing at least one of bubbling dried air from the moisture trap through the hydrogen peroxide solution in the container for producing a hydrogen peroxide vapor, and passing dried air from the moisture trap into a headspace above a hydrogen peroxide solution in a container for producing a hydrogen peroxide vapor; estimating a concentration of hydrogen peroxide in the hydrogen peroxide vapor; and using the hydrogen peroxide vapor.

Other aspects and embodiments of the present invention will become apparent from the following detailed description, which, when taken in conjunction with the drawings, illustrate by way of example the principles of the invention.

DETAILED DESCRIPTION

Figure 1:
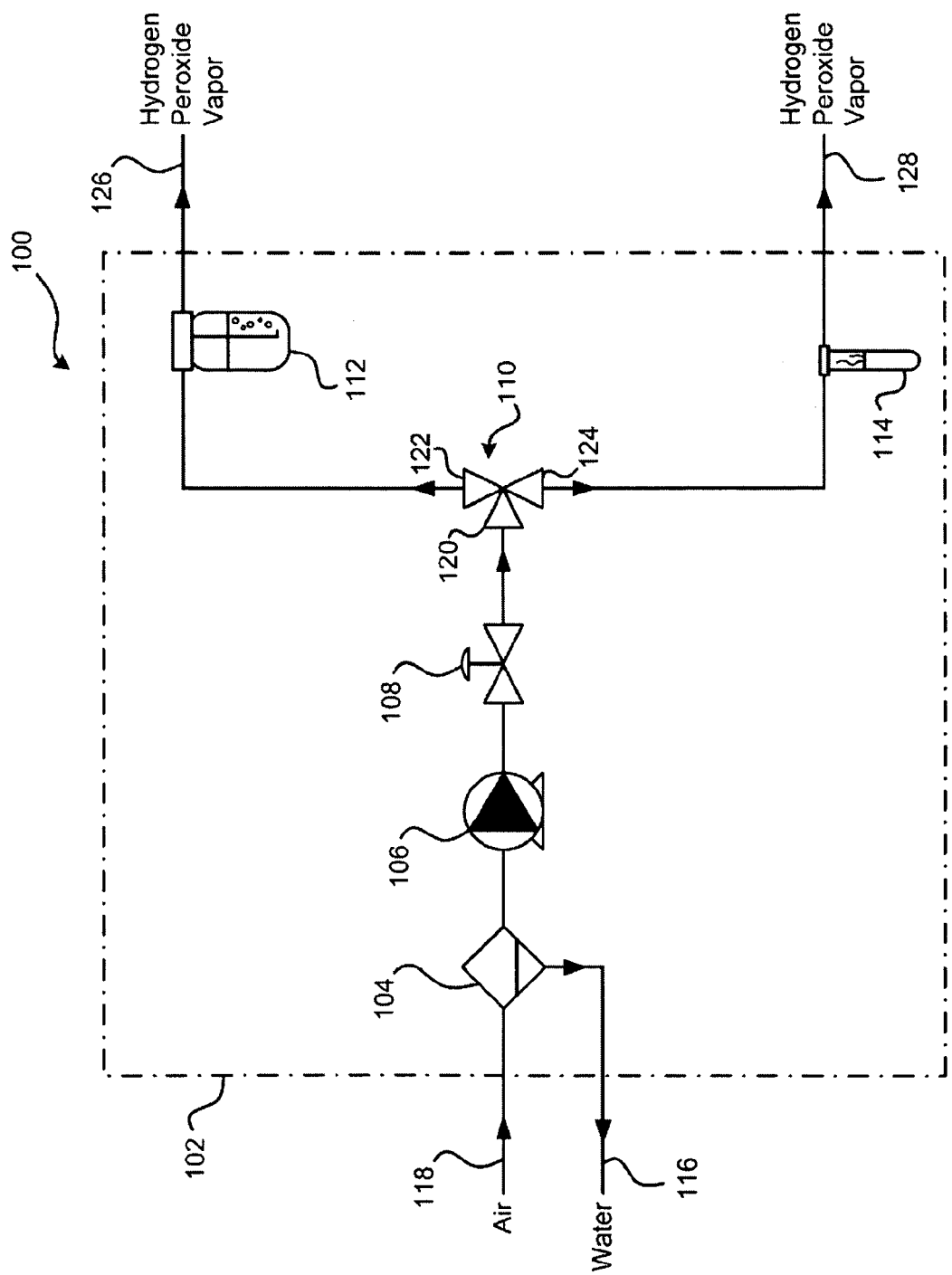
FIG. 1 is a schematic diagram of a hydrogen peroxide vapor generator system according to one embodiment.

The following description is made for the purpose of illustrating the general principles of the present invention and is not meant to limit the inventive concepts claimed herein. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc.

It must also be noted that, as used in the specification and the appended claims, the singular forms "a," "an" and "the" include plural referents unless otherwise specified.

In one general embodiment, a system comprises a moisture trap for drying air; at least one of a first container and a second container; and a mechanism for at least one of: bubbling dried air from the moisture trap through a hydrogen peroxide solution in the first container for producing a hydrogen peroxide vapor, and passing dried air from the moisture trap into a headspace above a hydrogen peroxide solution in the second container for producing a hydrogen peroxide vapor.

In another general embodiment, a hydrogen peroxide vapor generator comprises a moisture trap for drying air; a first aqueous hydrogen peroxide solution container having an inlet fluidically in line with the moisture trap to receive dry air therefrom by being bubbled through the aqueous hydrogen peroxide solution for producing higher concentration hydrogen peroxide vapor, and an outlet for availing the higher concentration hydrogen peroxide vapor; a second aqueous hydrogen peroxide solution container having an inlet fluidically in line with the moisture trap to receive dry air therefrom by being flowed into a headspace above the aqueous hydrogen peroxide solution for producing lower concentration hydrogen peroxide vapor, and an outlet for availing the lower concentration hydrogen peroxide vapor; and a switch valve for selectively channeling the dry air flow to at least one of the first and second containers.

In another general embodiment, a method comprises at least one of bubbling dried air through a hydrogen peroxide solution in a container for producing a first hydrogen peroxide vapor, and passing dried air from the moisture trap into a headspace above the hydrogen peroxide solution in a container for producing a second hydrogen peroxide vapor.

In another general embodiment, a method comprises adding a hydrogen peroxide solution to a container; causing at least one of bubbling dried air from the moisture trap through the hydrogen peroxide solution in the container for producing a hydrogen peroxide vapor, and passing dried air from the moisture trap into a headspace above a hydrogen peroxide solution in a container for producing a hydrogen peroxide vapor; estimating a concentration of hydrogen peroxide in the hydrogen peroxide vapor; and using the hydrogen peroxide vapor.

Now referring to FIG. 1, a small, portable, and rugged hydrogen peroxide vapor generation system 100 may include all or some of the elements shown. The system may be contained within an enclosure 102, such as a metal box with a handle, a plastic impact resistant suitcase, a rigid framework to secure each component, a housing designed for each component allowing easy access, etc.

The system 100 may include an air inlet 118 which may be connected to a moisture trap 104 via flexible tubes, rigid tubes, or pipes, constructed from such materials as polyvinyl chloride (PVC), nylon, polyethylene (PE), fluoropolymer such as polytetrafluoroethylene (PTFE), silicone, carbon steel, stainless steel, copper, aluminum, etc., which pass flow from the air inlet 118 through the moisture trap 104. The moisture trap 104 may be comprised of a condenser, column comprising DRIERITE® desiccants (comprised primarily of gypsum, otherwise known as calcium sulfate), or some other method of removing moisture from the air entering the air inlet 118. Generally, the moisture trap 104 may function to eliminate or substantially reduce humidity fluctuations in the dried air, and to remove nominally all of tile moisture in the inlet air.

In some embodiments, an absolute humidity of the air exiting the moisture trap 104 may be less than about 5.0 gram of water per cubic meter of the air, more preferably less than about 1.0 g/m$^3$, even more preferably less than about 0.5 g/m$^3$.

Air entering the air inlet may be ambient air drawn from the surrounding atmosphere, artificial mix of gases, commercially available gas, etc. The moisture trap 104 may have an outlet 116 to dispel trapped water. In other approaches, a removable hatch may provide access to the desiccant for replacement thereof. In addition, the air inlet 118 may have an inline filter (not shown) to trap particles and unwanted debris before it reaches the rest of the system 100.

Tubes or pipes, of such material as described above, may connect the moisture trap 104 to a pump 106. Any pump capable of producing desired maximum flow rates of air may be used, such as a peristaltic pump, positive displacement pump, centrifugal pump, impeller, blower, fan, etc., but a small, energy efficient 12 volt pump with standard electrical connections is particularly preferred. The pump 106 may be constant speed or variable speed, and also may be connected to a variable frequency drive (VFD) or some other device capable of controlling the speed of the pump, such that the air flow rate through the pump may be controlled. Generally, if a pump with a VFD is used, a control valve 108 may not be included in the system 100, as flow may be controlled without the use of the control valve 108.

In some preferred embodiments, the system 100 may be capable of providing a volumetric flow rate of about one liter per minute or less of the dried air. In some embodiments, this flow rate may be controlled by the pump 106, control valve 108, or combination of both.

With continued reference to FIG. 1, the pump 106 may be connected to a control valve 108 via additional tubes or pipes of such materials as described above. The control valve 108 may be automatically or manually adjustable to control the flow of air through the system 100. Automatic adjustment may be capable through feedback from a flow meter (not shown), possibly installed inline near the pump 106 outlet. In addition, a user input may be provided to set the desired flow rate, such that feedback, feedforward, or more complex control algorithms may be used to control the actual flow of air, as is understood by one skilled in the relevant art. Also, the control valve 108 may be self-regulated, such as a flow regulator, and may be manually adjusted to the desired flow rate, upstream pressure, downstream pressure, etc. The control valve 108 may be connected via tubes or pipes of such materials as described above to a switching valve 110, such as a three-way valve, which is capable of directing flow from a common inlet 120 into one of two outlets 122, 124. Outlet 122 may be connected to a first container 112, while outlet 124 may be connected to a second container 114. The outlets 120, 124 may be connected to the containers 112, 114 via tubes or pipes, of such material as described above.

The first container 112, which is sometimes referred to as a bubbler source, and which is particularly preferred for producing higher concentrations of hydrogen peroxide vapor, may be comprised of an aqueous solution comprising hydrogen peroxide. The first container 112 may include an inlet fluidically in line with the moisture trap 104 to receive dry air therefrom by being bubbled through the aqueous hydrogen peroxide solution for producing higher concentration hydrogen peroxide vapor, and an outlet for availing the higher concentration hydrogen peroxide vapor.

In some experiments, reagent grade 30% (by weight) hydrogen peroxide was mixed with various volumes of distilled water to produce various concentrations of hydrogen peroxide solution, including 30%, 0.001%, and other concentrations in between. Of course, any concentration of hydrogen peroxide solution may be used depending on the desired hydrogen peroxide vapor concentration, including concentrations higher than 30%, e.g., 50%, 70%, etc.

In some embodiments, the first container 112 may be comprised of a vessel, at least partially filled with an aqueous solution comprising hydrogen peroxide, with the air inlet tube or pipe extending below the surface of the aqueous solution contained therein. In some embodiments, the vessel may be 20 mL threaded vial, but could be any size or shape. An additional tube or pipe may protrude from above the aqueous solution inside the container, such that the vapor generated by bubbling the air through the aqueous solution may flow out this additional tube or pipe and continue toward the high concentration vapor outlet 126 of the system 100. As the air stream bubbles through the aqueous solution, it mixes with at least hydrogen peroxide contained within the aqueous solution, such that the expelled gas contains some amount of hydrogen peroxide vapor.

In preferred embodiments, the high concentration vapor outlet 126 and other equipment in contact with the hydrogen peroxide and its vapor may be comprised of materials suitable for use with low concentration hydrogen peroxide that are substantially nonreactive, such that corrosion and degradation of the materials is reduced, such as aluminum, stainless steel, PTFE, acrylonitrile butadiene styrene (ABS), ethylene propylene diene monomer (EPDM), nickel-alloys, etc.

The second container 114, which is sometimes referred to as a headspace source, and which is particularly preferred for producing lower concentrations of hydrogen peroxide vapor, may be comprised of an aqueous solution comprising hydrogen peroxide. The second container 114 may include an inlet fluidically in line with the moisture trap 104 to receive dry air therefrom by being flowed into a headspace above the aqueous hydrogen peroxide solution for producing lower concentration hydrogen peroxide vapor, and an outlet for availing the lower concentration hydrogen peroxide vapor.

In some embodiments, the second container 114 may be comprised of a vessel, at least partially filled with an aqueous solution comprising hydrogen peroxide, in which the air stream may pass above and out of the second container 114 toward the low concentration vapor outlet 128 of the system 100. As the air stream passes above the aqueous solution, it mixes with at least hydrogen peroxide vapor in the headspace above the aqueous solution, such that the expelled gas contains some amount of hydrogen peroxide vapor. In some embodiments, the vessel may be a threaded 2 mL vial, but could be any size or shape.

In preferred embodiments, the low concentration vapor outlet 128 and other equipment in contact with the hydrogen peroxide and its vapor may be comprised of materials suitable for use with low concentration hydrogen peroxide that are substantially nonreactive, such that corrosion and degradation of the materials is reduced, such as aluminum, stainless steel, PTFE, ABS plastic, EPDM, nickel-alloys, etc.

In some embodiments, the first container 112 and the second container 114 may be included in the same combined source apparatus, such that when higher concentrations of hydrogen peroxide vapor are desired, the air stream is bubbled through the aqueous solution comprising hydrogen peroxide such that the air stream upon exiting the combined source comprises hydrogen peroxide vapor. Further, when lower concentrations of hydrogen peroxide are sought, the air stream may be passed above the aqueous solution comprising hydrogen peroxide such that a portion of the air stream after passing through the combined source comprises hydrogen peroxide vapor. A switching valve may be included to direct the air stream flow through the space above the aqueous solution, or through the aqueous solution, depending on the concentration of hydrogen peroxide vapor desired.

In some embodiments, only one source is included in the system 100, such that only high or low concentrations of hydrogen peroxide vapor may be produced by the system 100.

In some embodiments, hydrogen peroxide vapor exiting the first container 112 and/or the second container 114 may have a hydrogen peroxide concentration of less than about 1000 parts per million (ppm) and greater than 0 ppm, in other approaches less than about 500 ppm, less than about 100 ppm, less than about 10 ppm, less than about 1 ppm, less than about 100 parts per billion (ppb), less than about 10 ppb, etc.

To enable simple and efficient replacement of the containers for the first container 112 and the second container 114, the vessels and accompanying apparatus may be designed such that each vessel may be unscrewed from the apparatus, with a new or the refilled vessel screwed in place of the expended or depleted vessel. The vessels and accompanying apparatus may be designed such that the aqueous solution contained therein is not exposed to the atmosphere, but may be exposed to the air stream once the vessel is installed in the accompanying apparatus. In some embodiments, the aqueous solutions in each container 112, 114 are comprised of the same constituents, for example of the same vol. % hydrogen peroxide and water, or are of different compositions.

The system 100 may comprise one inlet 118 for air, along with possibly multiple outlets, e.g., one outlet 116 for water expulsion from the moisture trap 104, one outlet 126 for high concentration vapor, and one outlet 128 for low concentration vapor. In another embodiment, the low and high concentration outlets 126, 128 may be included in a single outlet, such that the tubes or pipes leading from the first container 112 and the second container 114 converge, possibly through a three-way valve (not shown) such that only one source may outlet vapor at any one time. Each component of the system 100 may be removed or altered to fit specific operating conditions and goals for each specific application, and more or less components may comprise the system 100. In some embodiments of the system 100, the tubes or pipes may be substituted with direct connections between the elements of the system 100, such as connecting the outlet of the moisture trap 104 directly to the inlet of the pump 106. The flow rates of air through the system 100, amount of hydrogen peroxide in the aqueous solutions, composition of the inlet air, etc., may be changed to produce specific concentrations of high and/or low concentration vapor as desired by the operator.

In some embodiments, a method of producing hydrogen peroxide vapor includes at least one of bubbling dried air through a hydrogen peroxide solution in a container for producing a first hydrogen peroxide vapor, and passing dried air from the moisture trap into a headspace above the hydrogen peroxide solution in a container for producing a second hydrogen peroxide vapor. The method may be performed by any of the systems disclosed herein or any other architecture. Again, only the first or the second container may be present in some embodiments, while both may be present in other embodiments. Moreover, the same container may be used to produce the first and second hydrogen peroxide vapors.

In some embodiments, a pressure differential may be created, e.g., between the system and an ambient atmosphere, between components of the system, etc., for causing the dried air to pass from a moisture trap to the container or containers.

In some approaches, the dried air may have a volumetric flow rate of about one liter per minute or less. In some other approaches, the hydrogen peroxide vapor exiting the container or containers may have a hydrogen peroxide concentration of less than about 1000 parts per million. In more approaches, an absolute humidity of the air exiting the moisture trap may be less than about 1 gram per cubic meter of the air.

In some more approaches, an absolute humidity of the air exiting the moisture trap may be less than about 1 gram per cubic meter of the air.

Figure 2:
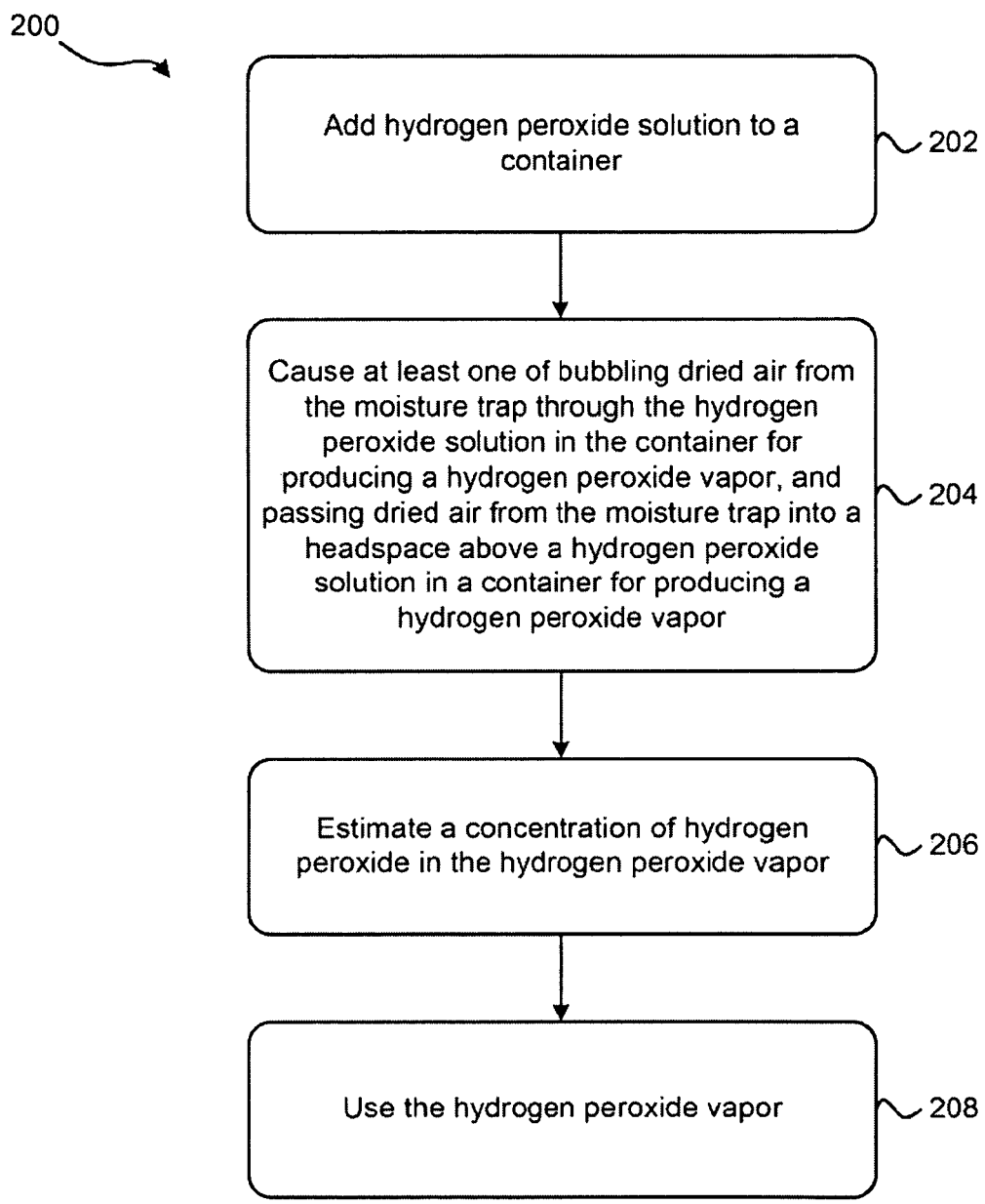
FIG. 2 is a flowchart of a method for producing hydrogen peroxide vapor according to one embodiment.

Now referring to FIG. 2, a method 200 for producing hydrogen peroxide vapor is shown. This method may be used in the context and functionality of FIG. 1. Of course, method 200 may be used in any desired environment, and is not to be limited in any way by reference to FIG. 1. In addition, any of the aforementioned definitions may apply in this description of method 200.

With continued reference to FIG. 2, in operation 202, a hydrogen peroxide solution may be added to a container. A container may comprise one or more containers, and the hydrogen peroxide solution may comprise other components other than hydrogen peroxide, such as water, solute, mixing agent, etc.

In operation 204, at least one of the following may be performed. First, bubbling dried air from the moisture trap may be caused through the hydrogen peroxide solution in the container for producing a hydrogen peroxide vapor. Second, dried air from the moisture trap may be passed into a headspace above a hydrogen peroxide solution in a container for producing a hydrogen peroxide vapor. Either or both of these actions may be performed.

In operation 206, a concentration of hydrogen peroxide in the hydrogen peroxide vapor may be estimated using any method, including methods well known to those skilled in the art such as bubbling the vapor through a N,N-dimethyl-p-phenylenediamine (DMP) colorimetric solution, with known flow rate and time, etc. The DMP calorimetric technique for vapor estimation is described for example only, and in no way limits the techniques which may be used to estimate the concentration of hydrogen peroxide vapor. In addition, one or more vapor concentration techniques may be used in combination, such that an average of one or more estimations may be used.

In operation 208, the hydrogen peroxide vapor may be used. For example, the hydrogen peroxide vapor may be used by contacting the hydrogen peroxide vapor with a hydrogen peroxide detector to test the hydrogen peroxide vapor detector's calibration and accuracy, to test the security measures at an airport security checkpoint using hydrogen peroxide vapor detectors, etc.

In some embodiments, the contact of the hydrogen peroxide vapor with the hydrogen peroxide vapor detector may be intermittent, i.e., periodic, episodic, random short or long bursts, etc., over a predetermined period of time. In other embodiments, the contact may be constant over a predetermined period of time, which may be a long or short period of time. The entire data set produced from these intermittent or constant contacts may be used to determine if the detector is accurately calibrated and capable of detecting the concentration of hydrogen peroxide used in the testing process.

While various embodiments have been described above, it should be understood that they have been presented by way of example only, and not limitation. Thus, the breadth and scope of a preferred embodiment should not be limited by any of the above-described exemplary embodiments, but should be defined only in accordance with the following claims and their equivalents.

What is claimed is:

1. A system, comprising:
   an air inlet leading into a housing, the air inlet being in fluidic communication with a moisture trap for drying air;
   a first container and a second container in the housing, each container being in fluidic communication with the moisture trap; and
   a mechanism in the housing for at:
      bubbling dried air from the moisture trap through a hydrogen peroxide solution in the first container for producing a first hydrogen peroxide vapor, and
      passing dried air from the moisture trap into a headspace above a hydrogen peroxide solution in the second container for producing a second hydrogen peroxide vapor having a lower hydrogen peroxide concentration than the first hydrogen peroxide vapor.

2. The system of claim 1, further comprising:
   an air pump in the housing and in fluidic communication with the moisture trap, the first container and the second container for inducing air flow between the moisture trap and at least one of the first container and the second container; and
   a housing supporting the moisture trap, the air pump, the air inlet, the first container and the second container.

3. The system of claim 1, wherein an absolute humidity of air exiting the moisture trap is less than about 1 gram of water per cubic meter of the air exiting the moisture trap.

4. The system of claim 1, further comprising a switching valve for selectively channeling the dried air flow to at least one of the first container and the second container.

5. The system of claim 1, wherein the housing supports: the moisture trap; the first container; and the second container.

6. The system of claim 1, the mechanism is further adapted for selectively bubbling dried air from the moisture trap through the hydrogen peroxide solution in the first container for producing the first hydrogen peroxide vapor, and for selectively passing dried air from the moisture trap into a headspace above the hydrogen peroxide solution in the first container for producing a third hydrogen peroxide vapor having a lower hydrogen peroxide concentration than the first hydrogen peroxide vapor.

7. The system of claim 1, wherein an outlet of at least one of the first container and the second container includes a nonreactive inner surface.

8. The system of claim 1, wherein the mechanism is capable of providing a volumetric flow rate of about one liter per minute or less of the dried air.

9. The system of claim 1, wherein at least one of the first and second hydrogen peroxide vapors has a hydrogen peroxide concentration of less than about 1000 parts per million.

10. The system of claim 1, wherein air entering the moisture trap is not recirculated from an outlet of the mechanism.

11. The system of claim 6, wherein the second hydrogen peroxide vapor has a lower hydrogen peroxide concentration than the third hydrogen peroxide vapor.

12. A system as recited in claim 1, wherein the first and second hydrogen peroxide vapors have a hydrogen peroxide concentration of less than about 10 parts per billion (ppb) and greater than about 0 ppb.

13. A system as recited in claim 1, wherein an absolute humidity of air exiting the moisture trap is less than about 0.5 grams of water per cubic meter of the air exiting the moisture trap.

14. A system as recited in claim 1, further comprising the hydrogen peroxide solution in the first container.

15. A system as recited in claim 1, further comprising:
   an air pump in the housing and in fluidic communication with the moisture trap the first container and the second container for inducing air flow between the moisture trap and the at least one of the first container and the second container;
   a housing supporting the moisture trap, the air pump, the air inlet, the first container and the second container; and
   a switching valve for selectively channeling the dried air flow to the first container and the second container,
   wherein an absolute humidity of air exiting the moisture trap is less than about 1 gram of water per cubic meter of the air exiting the moisture trap,
   wherein the mechanism is configured for:
      bubbling dried air from the moisture trap through the hydrogen peroxide solution in the first container for producing the first hydrogen peroxide vapor,
      passing dried air from the moisture trap into the headspace above the hydrogen peroxide solution in the second container for producing the second hydrogen peroxide vapor exiting the second container,
      selectively passing dried air from the moisture trap into a headspace above the hydrogen peroxide solution in the first container for producing a third hydrogen peroxide vapor having a lower hydrogen peroxide concentration than the first hydrogen peroxide vapor, wherein an outlet of at least one of the first container and the second container includes a nonreactive inner surface, wherein the mechanism is capable of providing a volumetric flow rate of about one liter per minute or less of the dried air, wherein the second hydrogen peroxide vapor has a lower hydrogen peroxide concentration than the first hydrogen peroxide vapor, and wherein at least one of the first and second hydrogen peroxide vapors has a hydrogen peroxide concentration of less than about 1000 parts per million and greater than about 0 parts per million.

16. A hydrogen peroxide vapor generator, comprising:
a moisture trap for drying air;
a first aqueous hydrogen peroxide solution container having an inlet fluidically in line with the moisture trap to receive dry air therefrom and positioned to direct the dry air to bubble through an aqueous hydrogen peroxide solution in the first aqueous hydrogen peroxide solution container for producing a higher concentration hydrogen peroxide vapor, and an outlet for availing the higher concentration hydrogen peroxide vapor;
a second aqueous hydrogen peroxide solution container having an inlet fluidically in line with the moisture trap to receive dry air therefrom and flowed into a headspace above an aqueous hydrogen peroxide solution in the second aqueous hydrogen peroxide solution container for producing a lower concentration hydrogen peroxide vapor, and an outlet for availing the lower concentration hydrogen peroxide vapor;
a switch valve for selectively channeling the dry air flow to at least one of the first and second containers; and
a housing supporting the moisture trap, the first aqueous hydrogen peroxide solution container, the second aqueous hydrogen peroxide solution container, and the switch valve.

17. The hydrogen peroxide vapor generator of claim 16, further comprising:
an air pump fluidically inline with the moisture trap and the first and second containers for inducing air flow therebetween; and
an air inlet leading into the housing and fluidically connected to the moisture trap,
wherein the housing further supports the air pump and the air inlet.

18. The hydrogen peroxide vapor generator of claim 16, further comprising:
a flow control valve for controlling the rate of dry air flow to at least one of the first and second containers.

19. The hydrogen peroxide vapor generator of claim 16, further comprising:
PTFE tubing fluidically interconnecting the components of the hydrogen peroxide vapor generator.

20. The hydrogen peroxide vapor generator of claim 16, wherein air entering the moisture trap is not recirculated from an outlet of the hydrogen peroxide vapor generator.

21. A system as recited in claim 16, wherein an absolute humidity of air exiting the moisture trap is less than about 0.5 grams of water per cubic meter of the air exiting the moisture trap.

22. A system as recited in claim 16, further comprising the hydrogen peroxide solution in each of the containers.

* * * * *